(12) United States Patent
Lye et al.

(10) Patent No.: US 10,716,640 B2
(45) Date of Patent: Jul. 21, 2020

(54) ELECTRONIC ORIENTATION MONITOR AND AN ASSOCIATED METHOD

(71) Applicant: GYDER SURGICAL PTY LTD, New South Wales (AU)

(72) Inventors: Robert Lye, Brookvale (AU); William Hill, Brookvale (AU); Kim Lester, Brookvale (AU)

(73) Assignee: Gyder Surgical Pty Ltd., New South Wales (AU)

(*) Notice: Subject to any disclaimer, the term of this patent is extended or adjusted under 35 U.S.C. 154(b) by 0 days.

(21) Appl. No.: 15/950,444

(22) Filed: Apr. 11, 2018

(65) Prior Publication Data

US 2018/0311010 A1 Nov. 1, 2018

Related U.S. Application Data

(63) Continuation-in-part of application No. 14/408,616, filed as application No. PCT/AU2013/000713 on Jun. 28, 2013, now abandoned.

(30) Foreign Application Priority Data

Jun. 28, 2012 (AU) ................................ 2012902752
Apr. 12, 2013 (AU) ................................ 2013204920

(51) Int. Cl.
*A61B 90/00* (2016.01)
*A61B 5/00* (2006.01)
(Continued)

(52) U.S. Cl.
CPC ............ *A61B 90/06* (2016.02); *A61B 5/0082* (2013.01); *A61B 5/1071* (2013.01);
(Continued)

(58) Field of Classification Search
None
See application file for complete search history.

(56) References Cited

U.S. PATENT DOCUMENTS

2007/0032726 A1* 2/2007 Osaka .................. A61B 5/0048
600/459
2009/0254294 A1 10/2009 Dutta
(Continued)

FOREIGN PATENT DOCUMENTS

DE 20 2009 013604 2/2010
WO 02/080824 10/2002
(Continued)

OTHER PUBLICATIONS

Written Opinion and Search Report of the International Searching Authority, Australian Patent Office, Application No. PCT/AU2013/000713, dated Nov. 1, 2013.
(Continued)

*Primary Examiner* — Yanna Wu
(74) *Attorney, Agent, or Firm* — Gottlieb, Rackman & Reisman, P.C.

(57) ABSTRACT

The invention, in one aspect, provides an electronic orientation monitor. The monitor includes an orientation sensing electronics configured for calibration when in a reference orientation and being responsive to manipulation of the monitor so as to calculate first, second and third angles which together represent a difference between a current orientation of the monitor and the reference orientation. The monitor further includes a display being responsive to the first and second angles so as to display a point positioned relative to first and second axes, the display being further responsive to the third angle so as to display a line having a direction relative to the first and second axes such that a combination of the position of the point and the direction of
(Continued)

the line is indicative to a user of the difference between the current orientation of the monitor and the reference orientation.

24 Claims, 7 Drawing Sheets

(51) Int. Cl.
*A61B 8/08* (2006.01)
*A61B 5/107* (2006.01)
*A61B 5/1495* (2006.01)

(52) U.S. Cl.
CPC .......... *A61B 5/1072* (2013.01); *A61B 5/1495* (2013.01); *A61B 5/6823* (2013.01); *A61B 5/7445* (2013.01); *A61B 8/0858* (2013.01); *A61B 5/0086* (2013.01); *A61B 5/442* (2013.01); *A61B 2090/067* (2016.02); *A61B 2505/05* (2013.01); *A61B 2560/0223* (2013.01); *A61B 2562/0252* (2013.01)

(56) References Cited

U.S. PATENT DOCUMENTS

| | | |
|---|---|---|
| 2010/0076446 A1 | 3/2010 | Gorek |
| 2010/0172567 A1* | 7/2010 | Prokoski ............. A61B 5/0064 |
| | | 382/132 |
| 2011/0208093 A1 | 8/2011 | Gross et al. |
| 2012/0130279 A1* | 5/2012 | Stone .................... A61B 34/20 |
| | | 600/587 |
| 2012/0143268 A1* | 6/2012 | Burroughs ............. A61B 34/20 |
| | | 606/86 R |

FOREIGN PATENT DOCUMENTS

| | | |
|---|---|---|
| WO | 2003/037192 | 5/2003 |
| WO | 2004/112610 | 12/2004 |
| WO | 2005/046475 | 5/2005 |
| WO | 2010/031111 | 3/2010 |

OTHER PUBLICATIONS

International Preliminary Report of Patentability, Australian Patent Office, Application No. PCT/AU2013/000713, dated Oct. 8, 2014.
Extended European Search Report, European Patent Office, Application No. 13809703.5, dated Apr. 20, 2016.

* cited by examiner

ELECTRONIC ORIENTATION MONITOR AND AN ASSOCIATED METHOD

RELATED APPLICATIONS

This patent application is a continuation-in-part of U.S. patent application Ser. No. 14/408,616, filed on Dec. 17, 2014 which is a U.S. National Phase of PCT/AU2013/000713 filed Jun. 28, 2013 which claims priority to Australian Patent Application No. 2012902752 filed Jun. 28, 2012 and Australian Patent Application No. 2013204920 filed Apr. 12, 2013, which are hereby incorporated by reference in their entirety as part of the present disclosure.

FIELD OF THE INVENTION

The present invention relates to surgical implements and surgical methods and in particular to an electronic orientation monitor that may be used prior to and during surgical procedures, for example surgery involving prosthetic components.

BACKGROUND

The discussion of the prior art within this specification is not, and should not be taken as, an admission of the extent of common general knowledge in the field of the invention. Rather, the discussion of the prior art is provided merely to assist the addressee to understand the invention and is included without prejudice.

Whilst the following discussion is with respect to hip replacement surgery, a person skilled in the art will appreciate that the present invention is not limited to this particular field of use and may be adapted to use with any bone structure or various types of surgery.

Hip replacement surgery involves the use of a prosthetic cup (acetabular cup) or a prosthetic ball (femoral stems) or both to restore the ball and cup joint functionality of the hip. The ball and cup joint enables the hip to rotate in different directions to various degrees (in contrast to the relatively limited rotation of a knee joint).

Historically, hip replacement (arthroplasty) surgery required up to a 40 cm (7 to 12 inches) curved incision to provide sufficient access for the surgeon to manually access and manipulate the hip and femur. A prosthetic cup was attached to the hip socket or the head of the femur removed and replaced with a prosthetic ball, or both.

After the incision is made, the ligaments and muscles are separated to allow the surgeon access to the bones of the hip joint. It is typically this part of the surgery that makes the ligaments and muscles somewhat weak after surgery. Until they heal, which often takes about a month to six weeks, the patient must follow special hip precautions to prevent dislocation of the new hip joint.

Typical steps in hip replacement surgery include the following:

Removing the Femoral Head: Once the hip joint is entered, the femoral head is dislocated from the acetabulum. Then the femoral head is removed by cutting through the femoral neck with a power saw.

Reaming the Acetabulum: After the femoral head is removed, the cartilage is removed from the acetabulum using a power drill and a special reamer. The reamer forms the bone in a hemispherical shape to exactly fit the metal shell of the acetabular component.

Inserting the Acetabular Component: A trial component, which is an exact duplicate of the patient's hip prosthesis, is used to ensure that the joint received will be the right size and fit. Once the right size and shape is determined for the acetabulum, the acetabular component is inserted into place. In the uncemented variety of artificial hip replacement, the metal shell is simply held in place by the tightness of the fit or with screws to hold the metal shell in place. In the cemented variety, a special epoxy type cement is used to "glue" the acetabular component to the bone.

Preparing the Femoral Canal: To begin replacing the femoral head, special rasps are used to shape and hollow out the femur to the exact shape of the metal stem of the femoral component. Once again, a trial component is used to ensure the correct size and shape. The surgeon will also test the movement of the hip joint.

Inserting the Femoral Stem: Once the size and shape of the canal exactly fit the femoral component, the stem is inserted into the femoral canal. Again, in the uncemented variety of femoral component the stem is held in place by the tightness of the fit into the bone (similar to the friction that holds a nail driven into a hole drilled into wooden board with a slightly smaller diameter than the nail). In the cemented variety, the femoral canal is rasped to a size slightly larger than the femoral stem, then the epoxy type cement is used to bond the metal stein to the bone.

Attaching the Femoral Head: The metal ball that replaces the femoral head is attached to the femoral stem. The Completed Hip Replacement: Before the incision is closed, an x-ray is taken to make sure the new prosthesis is in the correct position.

Such surgery had a number of problems including:

a hospital stay of three days or more, post-operative pain and weeks of rehabilitation;

each cm of incision has a tenfold increase in the risks of blood clotting and infection post surgery; and the surgeon was reliant on his experience and eye to ensure accurate placement of the cup into the three dimensional hip socket and alignment of the cup with the ball/femur to enable proper function of the joint. Misalignment may lead to post operative complication such as misalignment of the leg, incorrect leg length and/or incorrect soft tissue tension. The long term effects of misaligned prosthetic components can also include accelerated wear of the components, aseptic loosening of the components and potentially early repetition of the surgery.

Attempts to overcome these problems include:

WO 2003/037192 which discloses a jig (impaction tool) for use in bone surgery and thus enables the use of a smaller incision. For hip replacement surgery, the jig enables the use of a 4 to 7 cm (2 to 3 inch) incision, i.e. keyhole surgery. Other benefits include a shorter stay in hospital, less blood loss, less pain, fewer postoperative dislocations and faster recovery; and WO 2005/046475 which discloses a gauge a gauge to assist the surgeon with accurate placement of a prosthetic when using a jig in keyhole surgery as the surgeon is no longer able to see the fit of the cup into the hip socket or the fit between the ball and cup.

The gauge provided in WO 2005/046475 has enabled efficient use of the impaction tool of WO 2003/037192. Commercial examples include the NilNav Hip System available from MAC Surgical. However, the gauge only works in two dimensions and there is still a heavy reliance on the surgeon's eye and experience for optimal placement of the cup into the hip.

A further attempt to overcome these problems was provided by WO 2010/031111, the contents of which are hereby incorporated in their entirety into this specification by way of cross reference. This prior art document discloses a brace (3) in the form of a clamp 20 that is attachable to a patient to define a reference point relative to the patient's anatomy for calibration of an electronic orientation monitor (2). It also discloses subsequent indications provided by a LED array (26) of the electronic orientation monitor (2), which may be used to assist in manipulation of a surgical implement (1). However, it has been appreciated by the present inventor that the information displayed by the LED array (26) of this prior art electronic orientation monitor (2) is limited in its extent and user friendliness.

Other limitations when using braces, jigs and referencing apparatus for surgical orientation relate to the physical differences between patients. Patients can have ectomorphic, endomorphic or mesomorphic bodies that provide varying levels of fat and flesh over surgical sites. As braces, jigs or referencing apparatus are placed on a patient to orient and use the surgical apparatus, they are affected by the varying flesh or fat layers over the proposed surgical site. This can lead to varied outcomes for the surgical orientation.

SUMMARY OF THE INVENTION

In one aspect of the present invention there is provided an electronic orientation monitor including:

orientation sensing electronics configured for calibration when in a reference orientation and being responsive to manipulation of the monitor so as to calculate first, second and third angles which together represent a difference between a current orientation of the monitor and the reference orientation; and a display being responsive to the first and second angles so as to display a point positioned relative to first and second axes;

wherein a coordinate of the position of the point on the first axis is determined with reference to the first angle and a coordinate of the position of the point on the second axis is determined with reference to the second angle, the display being further responsive to the third angle so as to display a line having a direction relative to the first and second axes such that a combination of the position of the point and the direction of the line is indicative to a user of the difference between the current orientation of the monitor and the reference orientation and wherein measurements of the soft tissue on the patient proximate the reference orientation are used to configure the orientation sensing electronics in the reference orientation.

Preferably, wherein the measurements of the soft tissue measure soft tissue thickness.

Preferably, force measurements are used to measure the thickness of the soft tissue.

Preferably, ultrasound transmission is used to measure the thickness of the soft tissue.

Preferably, infra-red dispersion measurements are used to measure the thickness of the soft tissue.

In one embodiment the first, second and third angles are respectively associated with a three dimensional reference system that is defined with reference to a roll angle, a pitch angle and a yaw angle. In this embodiment the monitor is configured during calibration to sense and store a reference roll angle, a reference pitch angle and a reference yaw angle.

Preferably the monitor is configured to calculate the first angle by sensing a current roll angle and comparing the reference roll angle to the current roll angle and it is configured to calculate the second angle by sensing a current pitch angle and comparing the reference pitch angle to the current pitch angle and it is configured to calculate the third angle by sensing a current yaw angle and comparing the reference yaw angle to the current yaw angle.

Preferably a coordinate of the position of the point on the first axis is determined with reference to the first angle and a coordinate of the position of the point on the second axis is determined with reference to the second angle. Also preferably the direction of the line is determined with reference to the third angle and the line extends from an origin of the first and second axes.

In one embodiment a correspondence between the current orientation and the reference orientation is indicated on the display by the point being disposed on an origin of the first and second axes and the line being aligned with a reference indicium.

Preferably the reference indicium is a predetermined one of the first or second axes. In this embodiment the point is indicated on the display as the point of intersection of two lines and the point is also indicated on the display by the centre of a circle. In this embodiment the display includes a numeric display of the first, second and third angles.

In another aspect of the present invention there is provided a method of guiding manipulation of an implement using an electronic orientation monitor as described above, the method including the steps of:

calibrating the electronic orientation monitor when in a reference orientation;

attaching the electronic orientation monitor to the implement; and manipulating the implement until the circle on the display of the electronic orientation monitor is positioned substantially on the origin of the first and second axes and the line on the display of the electronic orientation monitor is substantially aligned with the reference indicium so as to indicate that a current orientation of the monitor corresponds to the reference orientation.

The features and advantages of the present invention will become further apparent from the following detailed description of preferred embodiments, provided by way of example only, together with the accompanying drawings.

BRIEF DESCRIPTION OF THE ACCOMPANYING DRAWINGS

DETAILED DESCRIPTION OF PREFERRED EMBODIMENTS OF THE INVENTION

The electronic orientation monitor 1 includes orientation sensing electronics that are disposed within the casing shown in the figures. The details of an embodiment of the sensing electronics are disclosed in WO 2010/031111, the contents of which have been incorporated in their entirety into this specification by way of cross reference. The sensing electronics are calibrated when in the electronic orientation monitor 1 has been placed in a reference orientation. The brace disclosed in WO 2010/031111, or alternative braces and/or other referencing apparatuses and methods, may be used to place the electronic orientation monitor 1 into the reference orientation. Once in the reference orientation, the user presses the calibration button 2 and the monitor's processor causes the orientation sensing electronics to sense the reference orientation, which is stored in the monitor's random access memory. More particularly, the orientation sensing electronics generate data that is representative of three reference angles, which are respectively associated with a three dimensional reference system comprising a roll angle, a pitch angle and a yaw angle. Hence, upon calibration, the orientation sensing electronics senses data that is representative of a reference roll angle, a reference pitch angle and a reference yaw angle. Each of these angles is a component of the overall reference orientation and hence, together, these three angles define the reference orientation.

Soft tissue over the site of proposed surgery where the electronic orientation monitor 1 is to be used to calibrate provides an uneven surface and uneven thickness between the skin where the electronic orientation monitor 1 is operating. This unevenness can tilt the brace the orientation device 1 sits in by between 1 and 5.5 degrees which can result in a 0.7 degree of error of anteversion per degree of tilt. Taking into account the thickness of the soft tissue where the electronic orientation monitor 1 is to operate allows any tilt to be considered in the calculations of the orientation monitor 1.

Figure 4:
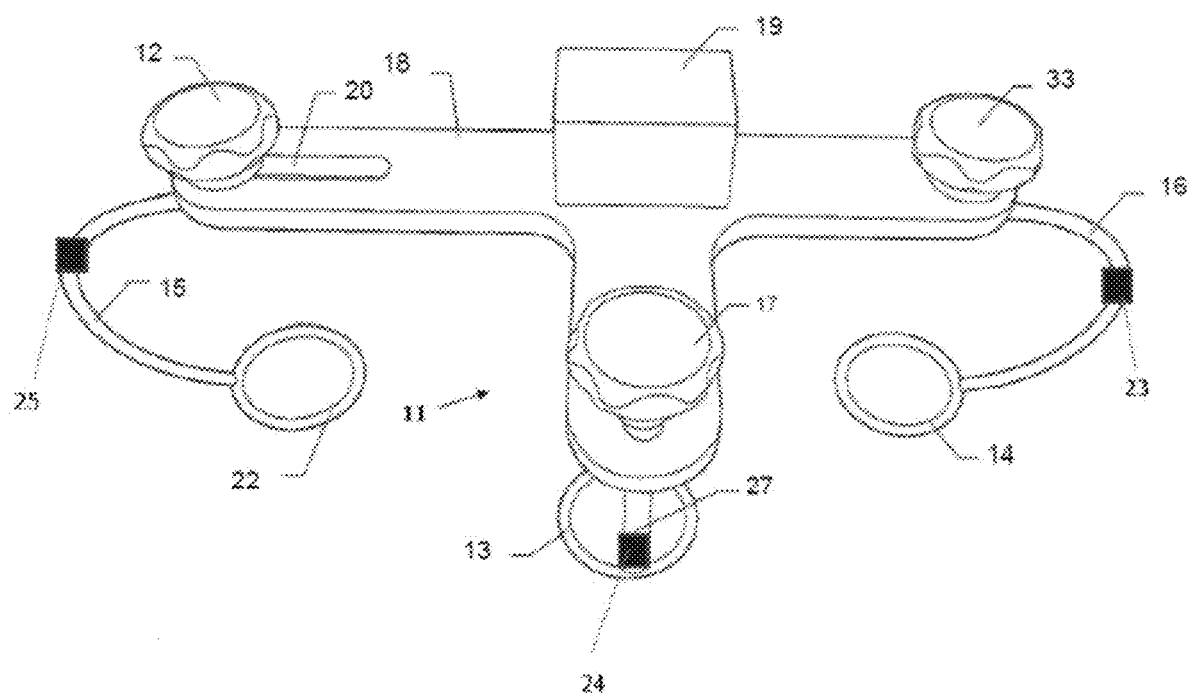
FIG. 4 is a top side perspective view of an embodiment of the force sensors according to the invention.
Figure 5:
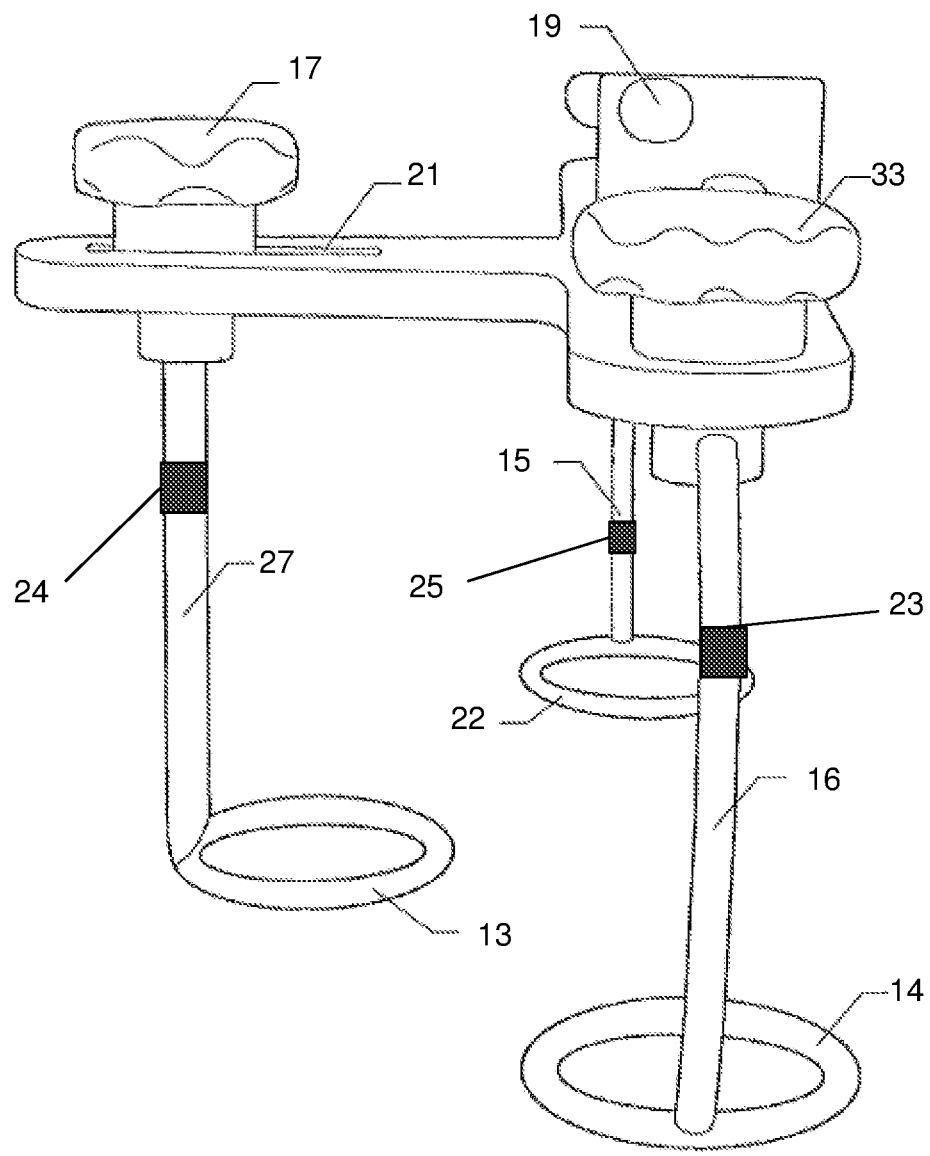
FIG. 5 is a top side perspective view of an embodiment of the force sensors according to the invention.

With reference to FIGS. 4 and 5, in one embodiment of the present invention force measurements are taken on the arms 15, 16 and 27 of the brace 11 the electronic monitor 1 is designed to sit within for reference measurements using force sensors 23, 24, 25. Measuring the force and adjusting the pressure applied to the patients skin so that the force is approximately equal on each arm 15, 16, 27 so that the layer of soft tissue underneath the arms is of approximately equal thickness. This minimises the tilt of the brace 11 and allows the electronic orientation monitor 1 to take accurate reference position readings.

The brace 11 of FIGS. 4 and 5 will be described in further detail. The skilled addressee will understand that alternative braces can be used, such as the one disclosed in WO 2010/031111 and fit within the scope of the present invention. The brace 11 has a 'T'-shaped frame 18 with a docking station 19 disposed at the intersection of the 'T' shape. The frame 8 defines two slots 20 and 21 disposed adjacent two of the extremities of the 'T' shape. Each of the slots 20 and 21 has a length of between 60 mm and 120 mm and in one embodiment each of their lengths is 70 mm and in another embodiment each of their lengths is 100 mm.

The brace 11 has three locating elements, which are each in the shape of circular loops 22, 13 and 14.

The first and third loops 22 and 14 are each attached to respective distal ends of arcuate members 15 and 16. Along the length of arcuate member s 15 and 16 are force sensors 25 and 23. The curvature of members 15 and 16 provides clearance for situations in which the referencing apparatus 1 is to be used on an overweight or obese patient having stomach fat deposits that would foul against the members 15 and 16 if they were straight. The proximal end of arcuate member 15 is attachable to the frame 18 at slot 20.

The proximal end of arcuate member 16 is attachable to the frame 18 at the extremity of the 'T' shaped frame 18 that does not have a slot 20 or 21. Rather, an aperture is disposed adjacent this extremity, through which the proximal end of arcuate member 16 extends.

If the user wishes to adjust the position of the first loop 22 relative to the frame 18, it is merely necessary to loosen the threaded fastener 12, then slide the proximal end of arcuate member 15 along slot 20 until the loop 22 is in the desired position, and then retighten the threaded fastener 12. This adjustability of the attachment position of the arcuate member 15 on the frame 18 allows the separation distance between loops 22 and 14 to be adjusted to match the separation distance between the patients left anterior superior iliac spine and the patient's right anterior superior iliac spine.

It will be appreciated that loosening of threaded fastener 12 also allows for rotation of arcuate member 15 about an axis of rotation that is orthogonal to the upper surface of the frame 8. Hence, if the user wishes to adjust the position of the clearance provided by the curvature of arcuate member 15, then the user merely loosens threaded fastener 12, rotates arcuate member 15 until the curvature is in the desired position and then retightens threaded fastener 12. Doing so does not re-position the loop 22 relative to the frame 8 because the centre of loop 22 is in axial alignment with the axis of rotation of the arcuate member 15. Similarly, it is possible to adjust the position of the clearance provided by the curvature of arcuate member 16 by loosening threaded member 33, rotating arcuate member 16, then re-tightening threaded member 33. This does not reposition loop 14 because its centre is in axial alignment with the axis of rotation of the arcuate member 16.

The second loop 13 is attached to the distal end of a linear elongate member 27. The proximal end of member 27 is attachable to the frame 18 at slot 21. The position of the second loop 13 can be adjusted by loosening threaded fastener 17, then sliding the proximal end of threaded fastener 17 until loop 13 is in the desired position and then re-tightening threaded fastener 17. In other words, the adjustability given by slots 20 and 21 allows the brace 1 to be used on patient's having variously sized pelvises.

Once the brace 11 is positioned readings from the force sensors 23, 24 and 25 can be taken. The attachment of the arms 15, 16 and 27 to the patient's body is adjusted until the force readings are approximately equal. This engagement, with approximately equal force readings, causes the docking station 19 to assume a reference orientation relative to the three predefined anatomical sites.

Figure 6:
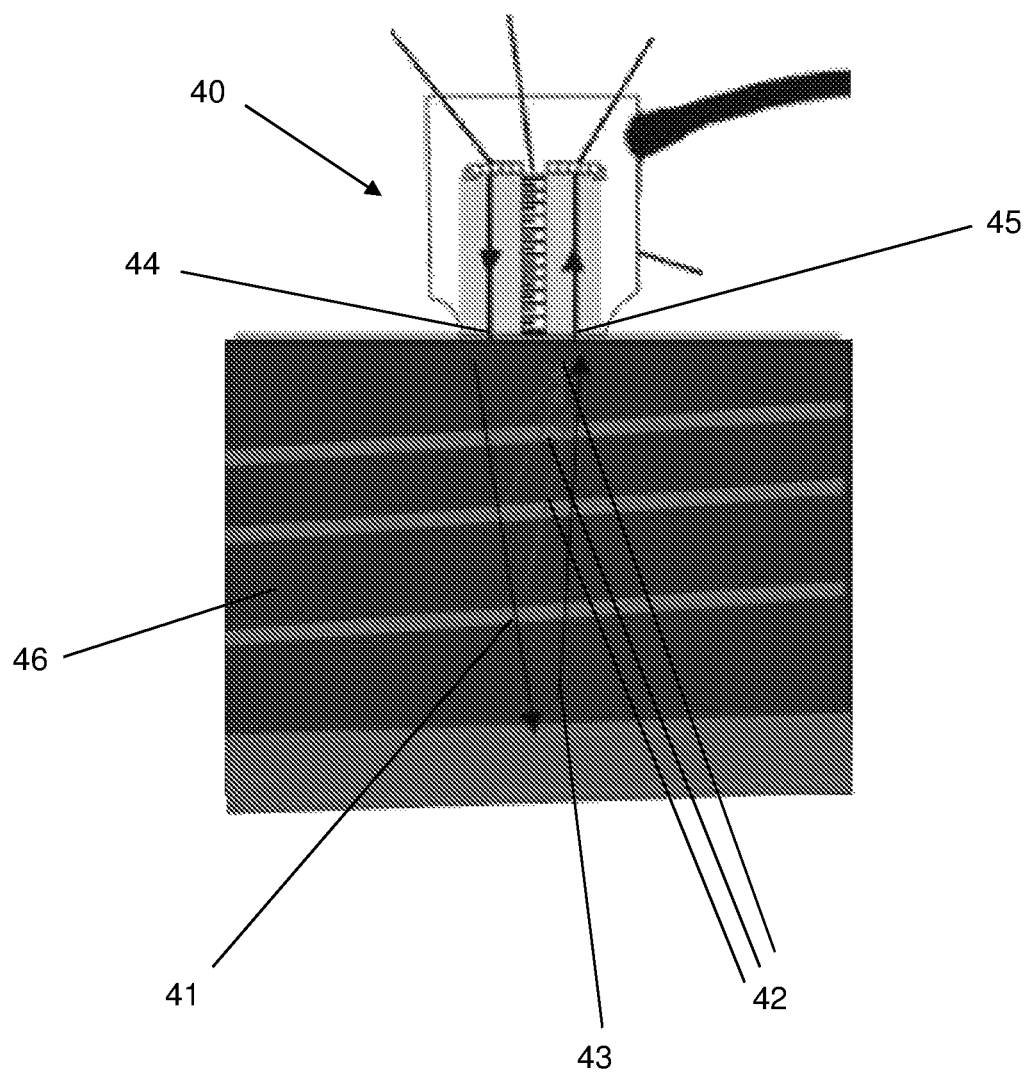
FIG. 6 is a side view of an ultrasound probe according to an embodiment of the present invention.

With reference to FIG. 6 a further embodiment of the present invention is illustrated that uses ultrasound to measure soft tissue 46 depth around the potential surgical site where the electronic orientation monitor 1 is to be calibrated and used. In this embodiment ultrasonic probes 40 are used to measure the thickness of soft tissue 46 around the proposed surgical site. A brace as mentioned above is placed around a patient and has three arms arranged to be placed around the surgical site. For a hip replacement these arms would be placed to be over the right Anterior Superior Iliac Spine (ASIS), the left Anterior Superior Iliac Spine (ASIS) and the pubic crest.

A type A ultrasound with an ultrasound frequency of between 2 and 20 MHz is used by the probe 40. The probe 40 transmits transmission ultrasound waves 41 through transmitter 44 into the soft tissue 46 and receives the reflected ultrasound waves 42 at receiver 43. The probe amplifies the signal received at the receiver 43 and sends it for signal processing by a computer processor. The thickness of the soft tissue 46 is defined with reference to the bone the soft tissue 46 lies over.

As the soft tissue 46 under the probe 40 is not uniform intermediate ultrasound echoes 42 are received by the receiver 43. As the bone is the furthest away object, the last echo signal 43 received is used to calculate the soft tissue 46 depth.

For a hip replacement using a three arm brace, ultrasound probes 40 are placed on all three arms to measure the thickness of the soft tissue 46 around the proposed surgical site where the electronic orientation monitor 1 is to be placed. With the differing thicknesses of the soft tissue 46 taken into account, the brace 11 can be adjusted to provide approximately equal soft tissue 46 thicknesses. Alternatively, the differing thicknesses can be used to take into account the tilt of the brace when providing the orientation reading.

Figure 7:
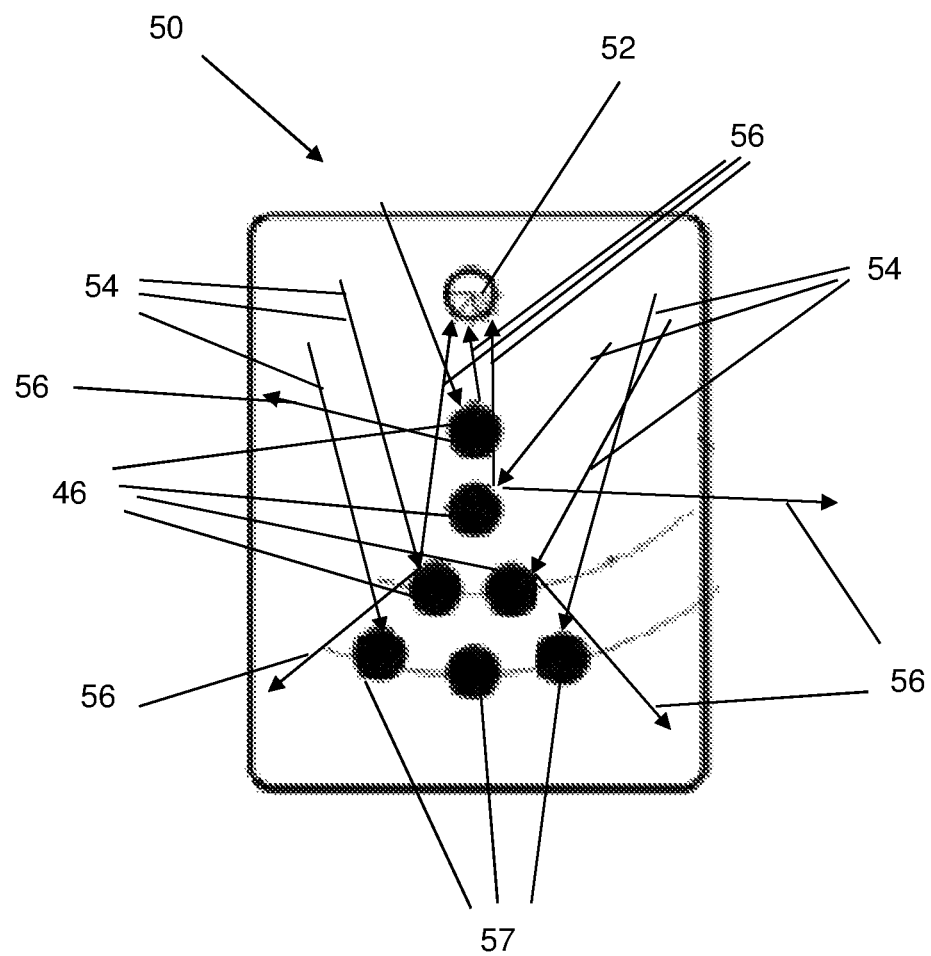
FIG. 7 is a plan view of an infrared detector according to an embodiment of the present invention.

With reference to FIG. 7 a further embodiment of the present invention is illustrated that uses and infrared detection system 50 to detect infrared dispersion and measure soft tissue 46 depth around the potential surgical site where the electronic orientation monitor 1 is to be calibrated and used.

Human tissue is somewhat translucent in the near infrared range. Between 800 and 950 nm soft tissue 46 scatters but does not absorb light. Bone 57 on the other hand has an absorption peak at 950 nm, absorbing light around this wavelength. Therefore incident light 54 that impacts soft tissue 46 is scattered as scattered light 56. Some of the scattered light 56 reflects back to a photodetector 52 that is at a known distance from the photodetector 52. The backscattered light 56 is received by the photodetector 52 and processed to calculate the distance the backscattered light 56 has travelled. This is then used to calculate the distance to the bone 57 and therefore the thickness of the soft tissue. With the thickness of the soft tissue 46 known, this thickness can be taken into account when orienting the electronic orientation monitor 1 as noted above with respect to FIG. 6. This can be displayed on a monitor to assist a surgeon align the electronic orientation monitor 1 correctly.

Once calibrated, the electronic orientation monitor 1 is typically detached from the referencing apparatus and then rigidly attached to a surgical implement such that the electronic orientation monitor I moves as one with the implement. As the electronic orientation monitor I is manipulated whilst attached to the implement, its orientation sensing electronics continue to generate data that is representative of current values for the roll angle, the pitch angle and the yaw angle. This data is communicated to the monitor's processor, which is programmed to compare the current values to the reference values so as to calculate first, second and third angles. More particularly, the processor subtracts the stored reference roll angle from the current roll angle to calculate the first angle, it subtracts the stored reference pitch angle from the current pitch angle to calculate the second angle. It subtracts the stored reference yaw angle from the current yaw angle to calculate the second angle. Together the first, second and third angles represent a difference between a current orientation of the monitor and the reference orientation.

The monitor's display 3 may take the form of any screen that can be driven by executable software instructions to display graphics. In some preferred embodiments it is a liquid crystal display and in some alternative embodiments it is an organic light-emitting diode display. The display 3 is used to present visual information to the user that is indicative of the first, second and third angles and which may therefore be used to help guide the monitor I into a desired orientation, for example towards the reference orientation. The visual information that is responsive to the first and second angles takes the form of a point 4 positioned relative to a first axis 5 (labeled the 'X' axis in the figures) and a second axis 6 (labeled the 'Y' axis in the figures). The visual information also takes the form of a line 7 that extends from the origin 8 of the first and second axes and 6 in a direction that is dependent upon the third angle. Hence, a combination of the position of the point 4 and the direction of the line 7 is indicative to a user of the difference between the current orientation of the monitor I and the reference orientation.

To assist the user to identify the point 4, it is indicated on the display 3 as the point of intersection of two lines 9 and 10. Additionally, it is indicated on the display as the centre of circle 11.

Figure 1:
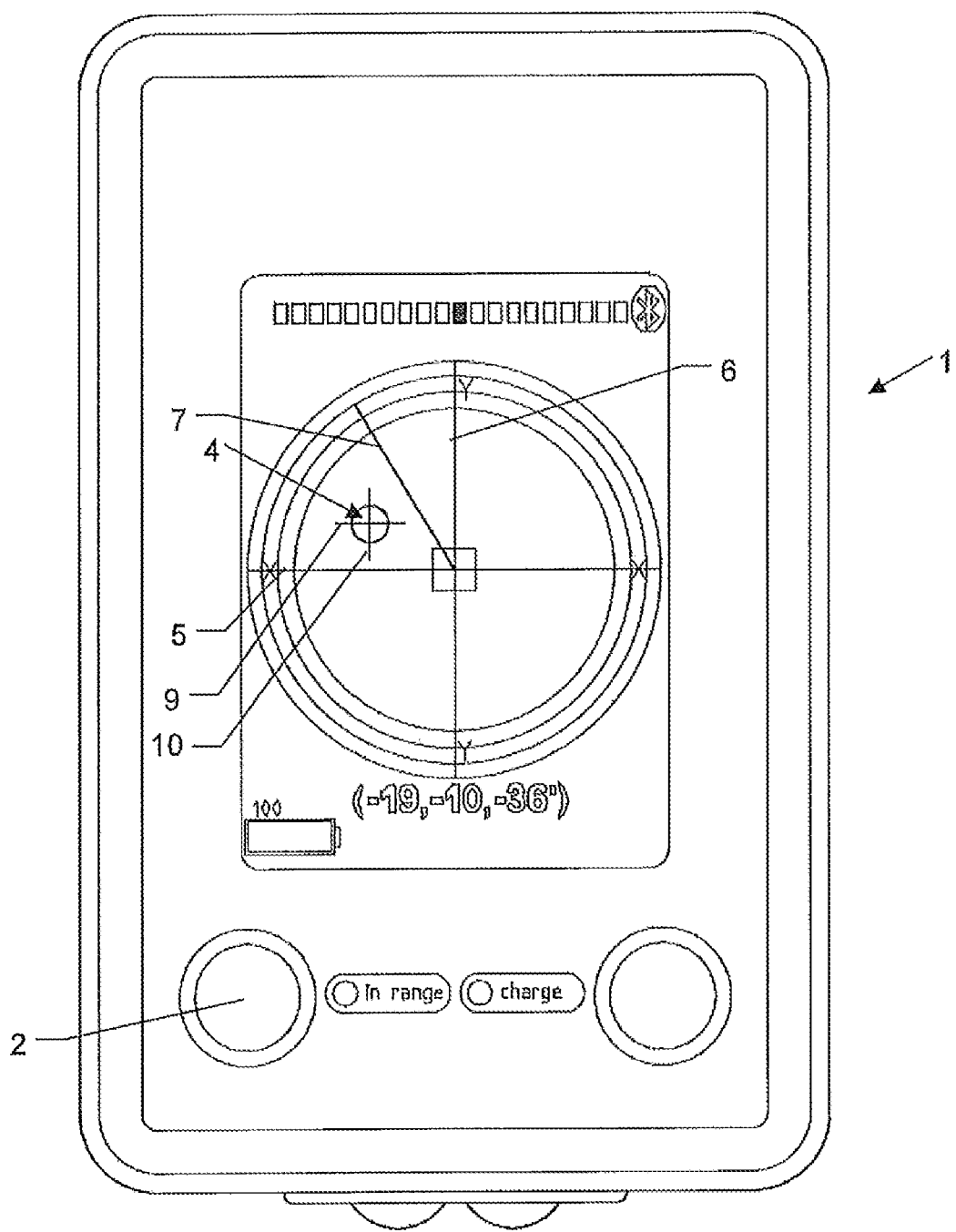
FIG. 1 is a plan view of an embodiment of the electronic orientation monitor according to the invention showing a display upon which an orientation that diverges from the reference orientation is depicted.
Figure 2:
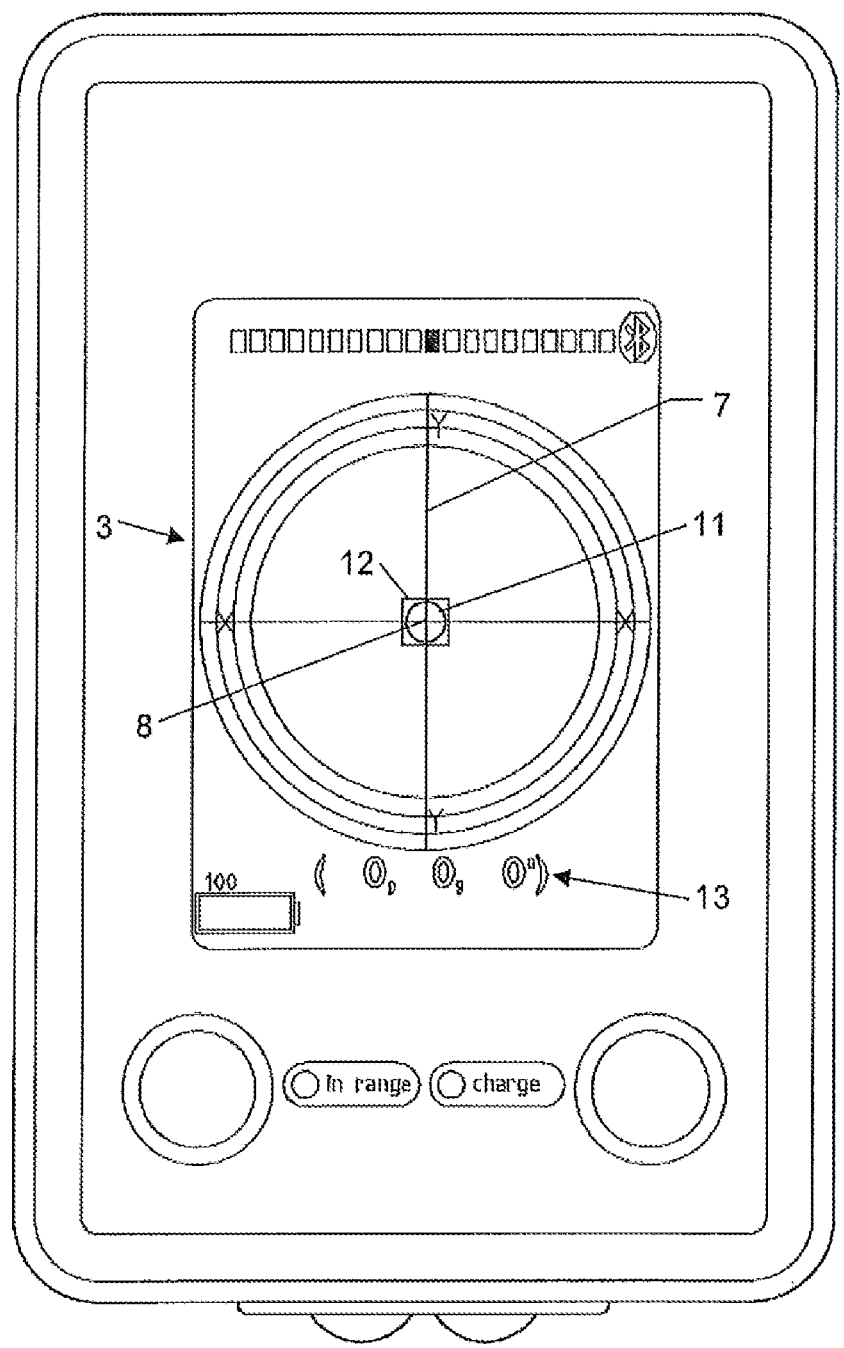
FIG. 2 is a plan view of the embodiment of FIG. 1 showing a display upon which an orientation that corresponds to the reference orientation is depicted.
Figure 3:
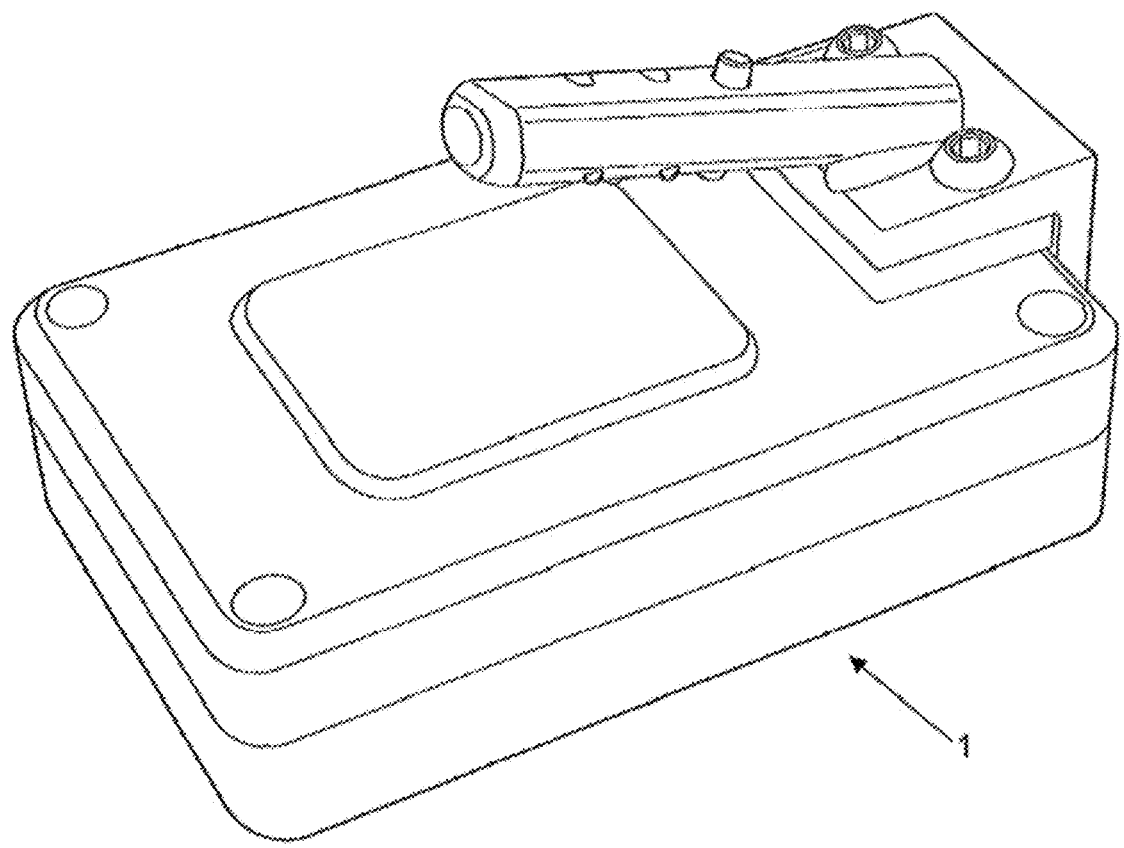
FIG. 3 is a bottom side perspective view of the embodiment of FIG. 1.

The monitor's processor is programmed with an algorithm or formula that is used to calculate the coordinates of the point 4 based on the first and second angles. In one embodiment, there is a linear relationship between the value of the first angle and the coordinate on the first axis 5 at which the point 4 is displayed. Similarly, in this embodiment there is a linear relationship between the value of the second angle and the coordinate on the second axis 6 at which the point 4 is displayed. Hence, if the first and second angles are each equal to zero, then the point 4 is displayed on the origin 8, as shown in FIG. 2. If the monitor 1 is manipulated such that the current value of the roll angle exceeds the reference roll angle, then the point 4 moves towards the right hand side of the display 3. If the monitor 1 is manipulated such that the current value of the roll angle is less than the reference roll angle, then the point 4 moves towards the left hand side of the display 3. If the monitor 1 is manipulated such that the current value of the pitch angle exceeds the reference pitch angle, then the point 4 moves towards the upper side of the display 3. If the monitor 1 is manipulated such that current value of the pitch angle is less than the reference pitch angle, then the point 4 moves towards the lower side of the display 3.

In another embodiment there is a non-linear relationship between the values of the first and second angles and the position at which the point 4 is displayed. This nonlinear relationship may be used to depict the position of the point 4 with high sensitivity at positions close to the origin 8 and with progressively less sensitivity at positions spaced away from the origin.

The direction in which the line 7 extends from the origin 8 is determined with reference to the third angle. More particularly, the direction of the line 7 is selected such that the included angle between the line 7 and the second axis 6 is equal to the third angle. Therefore, if the current yaw angle of the monitor 1 is equal to the reference yaw angle, then the line 7 lies directly on the second axis 6, as shown in FIG. 2. Hence, the second axis 6 is used as the reference indicium, however it will be appreciated that other indicia could be used as a reference indicium, such as the first axis 5 or another line or reference indicium that is displayed for this purpose.

The state of the point 4 and the line 7 as shown in FIG. 2, in which the point 4 is substantially disposed on the origin 8 and the line 7 is substantially aligned with the second axis 6, indicates to the user that the current orientation of the monitor 1 corresponds to the reference orientation. Hence, if a user is intending to orient the implement into the reference orientation, then the user simply manipulates the monitor 1 in three dimensions until the state of the point 4 and the line 7 as shown in FIG. 2 is displayed on the display 3.

A square 12 is depicted on the display 3 centered about the origin 8. The square 12 is sized such that the circle 11 fits neatly within it, as shown in FIG. 2. This assists the user to confirm that the point 4 is positioned on the origin 8. Additionally, when the point 4 is positioned on the origin 8, the lines 9 and 10 overlie the inner portions of the first and second axes 5 and 6, which also assists the user to confirm that the point 4 is on the origin 8.

The display 3 also includes a display that is a set 13 of three numbers, which are the first, second and third angles. This provides additional useful information for the user, particularly if the desired orientation differs from the reference orientation. For example, a user may decide that the desired orientation should differ from, say, the reference yaw angle by a particular angle, say 5. In this case, the user would manipulate the monitor 1 until the numeric reading shows (0, 0, 5).

While a number of preferred embodiments have been described, it will be appreciated by persons skilled in the art that numerous variations and/or modifications may be made to the invention without departing from the spirit or scope of the invention as broadly described. The present embodiments are, therefore, to be considered in all respects as illustrative and not restrictive.

The invention claimed is:

1. A system for calibrating a surgical electronic orientation monitor, the system comprising:
  a surgical electronic orientation monitor detachably engageable to a brace and a surgical implement;
  the brace usable for taking measurements for calibrating the surgical electronic orientation monitor for subsequent use with the surgical implement, the brace comprising:
  a rigid frame including a first elongated portion extending in a first direction and a second elongated portion extending in a second direction crossing the first direction, wherein the first and second elongated portions are connected to each other at a first frame connectioin point;
  a docking station to which the surgical electronic orientation monitor can be attached;
  first and second arcuate members connected to the first elongated portion at respective first and second member connection points with the first frame connection point being disposed between the first and second arcuate members,
  wherein a position of at least one of the first and second member connection points is adjustable, allowing the at least one of the first and second arcuate members to be selectively positioned along the first elongated portion such that a separation distance between the first and second arcuate members can be selectively set to accommodate a patient's body between the first and second arcuate members, and
  a third elongated member connected to the second elongated portion;
  a first force sensor disposed on the first arcuate member, a second force sensor disposed on the second arcuate member and a third force sensor disposed on the third elongated member;
  wherein distal ends of the first and second arcuate members and a distal end of the third elongated member are respectively configured to be placed over the patient's skin, the first, second and third force sensors providing force measurements indicative of the thickness of soft tissue in the vicinity of each respective arcuate member when the brace is mounted with the first and second arcuate members and the third elongated member at respective anatomical sites on a patient, the brace being adjustable to vary the force readings to place the docking station in a reference orientation relative to the respective anatomical sites for calibration of the surgical electronic orientation monitor when attached to the docking station.

2. The system of claim 1, further comprising a first loop disposed at the distal end of the first arcuate member and a second loop disposed at the distal end of the second arcuate member.

3. The system of claim 2, wherein the first arcuate member is rotatable about a first axis of rotation, the first axis of rotation being orthogonal to an upper surface of the frame.

4. The system of claim 3, wherein a center of the first loop is in axial alignment with the first axis of rotation.

5. The system of claim 1, further comprising:
  a slot extending at least partially along the first elongated portion; and
  a threaded fastener configured to be selectively slid along the slot, the slot and the threaded fastener together defining the first member connection point;
  wherein the first arcuate member is connected to the threaded fastener.

6. The system of claim 1, wherein the first and second elongated portions of the frame form a "T" shape.

7. The system of claim 1, wherein the surgical electronic orientation monitor comprises orientation sensing electronics configured for calibration when in the reference orientation and being responsive to manipulation of the surgical electonic orientation monitor so as to calculate first, second and third angles which together represent a difference between a current orientation of the surgical electronic orientation monitor and the reference orientation.

8. The system of claim 7, the surgical electronic orientation monitor further comprising a display and operable to output on the display indicia responsive to current values fo a roll angle, a pitch angle and a yaw angle of the surgical electronic orientation monitor relative to the reference orientation, the indicia usable to orient the surgical implement when the surgical electronic orientation monitor is rigidly attached to the surgical implement.

9. A system for calibrating a surgical electronic orientation monitor, the system comprising:
  a surgical electronic orientation monitor detachably engageable to a brace and a surgical implement;
  the brace usable for taking measurement for calibrating the surgical electronic orientation monitor for subsequent use with the surgical implement, the brace comprising:
  a rigid frame including a first elongated portion extending in a first direction and a second elongated portion extending in a second direction crossing the first direction, wherein the first and second elongated portions are connected to each other at a first frame connection point;
a docking station to which the surgical electronic orientation monitor can be attached;
first and second arcuate members connected to the first elongated portion at respective first and second member connection points with the first frame connection point being disposed between the first and second arcuate members;
wherein a position of at least one of the first and second member connection points is adjustable, allowing the at least one of the first and second arcuate members to be selectively positioned along the first elongated portion such that a separation distance between the first and second arcuate members can be selectively set to accommodate a patient's body between the first and second arcuate members;
a third elongated member connected to the second elongated portion;
a first ultrasound probe disposed on the first arcuate member, a second ultrasound probe disposed on the second arcuate member and a third ultrasound probe disposed on the third elongated member;
wherein distal ends of the first and second arcuate members and a distal end of the third elongated member are respectively configured to be placed over the patient's skin, the first, second and third ultrasound probes providing soft tissue measurements indicative of the thickness of soft tissue in the vicinity of each respective member when the brace is mounted with the first and second arcuate memebers and the third elongated member at respective anatomical sites on a patient, the brace being adjustable to vary the soft tissue measurements to place the docking statiion in a reference orientation relative to the respective anatomical sites for calibration of the surgical electronic orientation monitor.

10. The system of claim 9, further comprising a first loop disposed at the distal end of the first arcuate member and a second loop disposed at the distal end of the second arcuate member.

11. The system of claim 10, wherein the first arcuate member is rotatable about a first axis of rotation, the first axis of rotation being orthogonal to an upper surface of the frame.

12. The system of claim 11, wherein a center of the first loop is in axial alignment with the first axis of rotation.

13. The system of claim 9, further comprising:
a slot extending at least partially along the first elongated portion; and
a threaded fastener configured to be selectively slid along the slot, the slot and the threaded fastener together definging the first member connection point;
wherein the first arcuate member is connected to the threaded fastener.

14. The system of claim 9, wherein the first and second elongated portions of the frame form a "T" shape.

15. The system of claim 9, wherein the surgical electronic orientation monitor comprises orientaion sensing electronics configured for calibration when in the reference orientation and being respoinsive to manipulation of the surgical electronic orientation monitor so as to calculate first, second and third angles which together represent a difference between a current orientation of the surgical electronic orientation monitor and the referecne orientation.

16. The system of claim 15, the surgical electronic orientation monitor further comprising a display and operable to output on the display indicia responsive to currernt values for a roll angle, a pitch angle and a yaw angle of the surgical electronic orientation monitor relaitve to the reference orientation, the indicia usable to orient the surgical implement when the surgical electronic orientaton monitor is rigidly attached to the surgical impelment.

17. A system for calibrating a surgical electronic orientatioin monitor, the system comprising:
a surgical electron orientation monitor detachbly engageable to a brace and a surgical implement;
the brace usabe for taking measurement for calibrating the surgical electronic orientation monitor for subsequent use with the surgical implement, the brace comprising:
a rigid frame including a first elongated portion extending in a first direction and a second elongated portion extending in a second direction crossing the first direction, wherein the first and second elongated portions are connected to each other at a first frame connection point;
a docking station to which the surgical electronic orientation monitor can be attached;
first and second arcuate members connnected to the first elongated portion at respective first and second member connection points with the first frame connection point being disposed between the first and second arcuate member;
wehrein a postion of at least one of the first and second member connection points is adjustable, allowing the at least one of the first and second arcuate members to be selectively positioned along the first elongated portion such that a separation distance between the first and second arcuate members can be selectively set to accommodate a patient's body between the first and second arcuate members;
a third elongated member connected to the second elongated portion;
a first infrared photodetector disposed on the first arcutate member, a second infrared photodector disposed on the second arcuate member and a third infrared photodetector disposed on the third elongated member;
wherein distal ends of the first and second arcuate members and a distal end of the third elongated member are respectively configured to be placed over the patient's skin, the first, second and third infrared photodetectors providing soft tissue measurements indicative of the thickness of soft tissue in the vicinity of each respective member when the brace is mounted with the first and second arcuate members and the third elongated member at respective anatomical sites on a patient, the brace being adjustable to vary the soft measurements to place the docking station in a reference orientation relative to the respective anatomical sites for calibration of the surgical electronic orientation monitor.

18. The system of claim 17, further comprising a first loop disposed at the distal end of the first arcuate member and a second loop disposed at the distal end of the second arcuate member.

19. The system of claim 18, wehrein the first arcuate member is rotatable about a first axis of rotation, the first axis of rotation being orthogonal to an upper surface of the frame.

20. The sytstem of claim 19, wherein a center of the first loop is in axial alignment with the first axis of rotation.

21. The system of claim 17, further comprising:
a slot extending a least partially along the first elongated portion; and a threaded fastener configured to be selectively slid along the slot, the slot and the threaded fastener together difining the first member connnection point;

wehrein the first arcuate member is connected to the threaded fastener.

22. The system of claim 17, wherein the first and second elongate portions of the frame form a "T" shape.

23. The system of claim 17, wherein the surgical electronic orientation monitor comprises orientation sensing electronics configured for calibration when in the reference orientation and being responsive to manipulatioin of the surgical electronic orientation monitor so as to calculate first, second and third angles which together represent a difference between a current orientation of the surgical electronic orientation monitor and the reference orientation.

24. The system of claim 23, the surgical electronic orientation monitor further comprising a display and operable to output on the display indicia responsive to current values for a roll angle, a pitch angle and a yaw angle of the surgical electronic orientatin monitor relative to the reference orientation, the indicia usable to orient the surgical implement when the surgical electronic orientation monitor is rigidly attached to the surgical implement.

\* \* \* \* \*